(12) United States Patent
Holder

(10) Patent No.: US 10,912,904 B2
(45) Date of Patent: Feb. 9, 2021

(54) DETECTING COMBUSTION OF A NASAL CANNULA

(71) Applicant: KONINKLIJKE PHILIPS N.V., Eindhoven (NL)

(72) Inventor: Gary Nathan Holder, Ringgold, GA (US)

(73) Assignee: Koninklijke Philips N.V., Eindhoven (NL)

( * ) Notice: Subject to any disclaimer, the term of this patent is extended or adjusted under 35 U.S.C. 154(b) by 392 days.

(21) Appl. No.: 15/584,673

(22) Filed: May 2, 2017

(65) Prior Publication Data

US 2017/0319802 A1 Nov. 9, 2017

Related U.S. Application Data

(60) Provisional application No. 62/331,130, filed on May 3, 2016.

(30) Foreign Application Priority Data

Aug. 1, 2016 (EP) .................................... 16182199

(51) Int. Cl.
*A61M 16/06* (2006.01)
*A61M 16/20* (2006.01)
(Continued)

(52) U.S. Cl.
CPC .... *A61M 16/0087* (2013.01); *A61M 16/0003* (2014.02); *A61M 16/0666* (2013.01);
(Continued)

(58) Field of Classification Search
CPC .......... A61M 16/0003; A61M 16/0051; A61M 16/0087; A61M 16/0666; A61M 16/0672;
(Continued)

(56) References Cited

U.S. PATENT DOCUMENTS 5,335,305 A * 8/1994 Kosa .................. G01N 21/7703
156/154
5,676,154 A * 10/1997 Pettersson ............ A61B 5/0816
600/529

(Continued)

FOREIGN PATENT DOCUMENTS

DE 201012009706 U1 6/2013
EP 2371411 A1 10/2011
(Continued)

OTHER PUBLICATIONS

BPR Medical Gas Control, www.bprmedical.com Webpage Downloaded From the Internet Apr. 25, 2017.

*Primary Examiner* — Annette Dixon
(74) *Attorney, Agent, or Firm* — Daniel H. Brean

(57) ABSTRACT

A system includes a nasal cannula having a flexible tube configured to transmit oxygen gas to a user, an optical fiber coupled to the nasal cannula and configured to transmit light having a frequency spectrum range at least including that of light resulting from combustion of the nasal cannula while transmitting the oxygen gas to the user, a detector operatively coupled to the optical fiber and configured to detect the light transmitted through the optical fiber, and a valve. The valve is configured to be actuated to interrupt the transmission of the oxygen gas to the user through the nasal cannula in response to a signal from the detector.

26 Claims, 6 Drawing Sheets

(51) Int. Cl.
*A61M 16/08* (2006.01)
*A61M 16/00* (2006.01)

(52) U.S. Cl.
CPC .... *A61M 16/0672* (2014.02); *A61M 16/0875* (2013.01); *A61M 16/20* (2013.01); *A61M 16/0051* (2013.01); *A61M 2205/18* (2013.01); *A61M 2205/3306* (2013.01); *A61M 2205/3313* (2013.01); *A61M 2205/3337* (2013.01); *A61M 2205/364* (2013.01)

(58) Field of Classification Search
CPC .............. A61M 16/0875; A61M 16/20; A61M 2205/18; A61M 2205/3306; A61M 2205/3313; A61M 2205/3337; A61M 2205/364; A61M 16/00; A61M 16/04; A61M 16/0477; A61M 16/0486; A61M 16/0816; A61M 16/1075; A61M 2016/0039; A61M 2205/3368; A61M 2205/3606; A61M 2205/581; A61M 2205/583; A62C 3/00; G10L 17/26; H01L 2224/36; H01L 2224/37599; H01L 2224/376; H01L 2224/40; H01L 2224/40137; H01L 2224/83801; H01L 2224/84801; H01L 24/33; H01L 24/37; H01L 24/40; H01L 2924/00; H01L 2924/00012; H01L 2924/00014; H01L 2924/1305; H01L 2924/13055; H01L 2924/181; A61B 2017/00057; A61B 2017/00088; A61B 2017/00123; A61B 46/00; A61B 46/40; A61B 5/0002; A61B 5/0816; A61B 5/087; A61B 5/0873; A61B 5/097; A61B 5/16; A61B 5/4064; A61B 5/4803

See application file for complete search history.

(56) References Cited

U.S. PATENT DOCUMENTS

| | | | |
|---|---|---|---|
| 6,257,750 | B1 | 7/2001 | Strasser |
| 8,800,180 | B2 | 8/2014 | Ching et al. |
| 2004/0015092 | A1* | 1/2004 | Pettersson ......... A61M 16/0666 600/532 |
| 2008/0039715 | A1 | 2/2008 | Wilson |
| 2008/0066748 | A1 | 3/2008 | Felske |
| 2010/0280362 | A1 | 11/2010 | Li |
| 2010/0300708 | A1* | 12/2010 | Raphael ............ A61M 16/0486 169/54 |
| 2012/0078069 | A1* | 3/2012 | Melker ................ A61B 5/0836 600/340 |
| 2013/0299005 | A1* | 11/2013 | Enomoto .......... A61M 16/0816 137/78.1 |
| 2013/0340752 | A1 | 12/2013 | Landis |
| 2018/0243025 | A1* | 8/2018 | Smits ....................... A62C 3/00 |

FOREIGN PATENT DOCUMENTS

| | | |
|---|---|---|
| EP | 2524714 A1 | 11/2012 |
| EP | 2682149 A2 | 1/2014 |
| JP | 2011092379 A | 5/2011 |
| WO | WO2013132397 A1 | 9/2013 |

* cited by examiner

DETECTING COMBUSTION OF A NASAL CANNULA

CROSS-REFERENCE TO RELATED APPLICATIONS

This patent application claims the priority benefit under 35 U.S.C. § 119(e) of U.S. Provisional Application No. 62/331,130 filed on May 3, 2016, the contents of which are herein incorporated by reference.

BACKGROUND OF THE INVENTION

1. Field of the Invention

The present disclosure pertains to a method and an apparatus for detecting combustion of a nasal cannula while transmitting oxygen gas to a user.

2. Description of the Related Art

It is known, in the area of providing supplemental oxygen gas to patients in the home, that a risk of a nasal cannula being ignited and causing possible injury to the patient and/or damage to the patient surroundings. Even though training of the patients and the warning labels are used to warn against the fire hazards, patients often refuse to stop smoking while receiving oxygen therapy. In addition, many patients connect a 50 to 100 foot connector cannula to their oxygen concentrator to allow them to walk freely around their home, the patient may not always be aware of the connector cannula coming in contact with a fire hazard such as, for example, an electric space heater, a fireplace, or other heat sources in their homes.

There are solutions such as, for example, a valve (e.g., a FireSafe valve from BPR Medical Ltd. (http://www.bpr-medical.com/)) that may be inserted in series with the cannula. When the fire from the ignited cannula reaches this valve, it shuts off the flow of oxygen gas. This valve may help reduce the risk of the cannula continuing to burn, but, by the time the fire has reached the valve, damage may have already been done. Also, this valve does not take into account the most common reason for cannula fires in which a patient is smoking and allows the cigarette to come into contact with nasal area of the cannula. The burning cannula has to burn all the way to the valve before it can stop the flow of oxygen which can be up to four feet or more from the nasal end of the cannula. The valve also does not prevent a space heater from igniting the connector cannula at some point between the oxygen source and the valve, which could be 50 feet or more away from the patient.

SUMMARY OF THE INVENTION

Accordingly, it is an object of one or more embodiments of the present patent application to provide a system that includes a nasal cannula having a flexible tube configured to transmit oxygen gas to a user, an optical fiber coupled to the nasal cannula and configured to transmit light having a frequency spectrum range at least including that of light resulting from combustion of the nasal cannula while transmitting the oxygen gas to the user, a detector operatively coupled to the optical fiber and configured to detect the light transmitted through the optical fiber, and a valve. The valve is configured to be actuated to interrupt the transmission of the oxygen gas to the user through the nasal cannula in response to a signal from the detector.

It is another aspect of one or more embodiments of the present patent application to provide a method for detecting combustion of a nasal cannula while transmitting oxygen gas to a user. The method includes providing the nasal cannula, the nasal cannula having a flexible tube configured to transmit oxygen gas to a user; providing an optical fiber, the optical fiber being coupled to the nasal cannula and configured to transmit light having a frequency spectrum range at least including that of light resulting from combustion of the nasal cannula while transmitting the oxygen gas to the user; detecting, using a detector operatively coupled to the optical fiber, the light transmitted through the optical fiber; and actuating a valve to interrupt the transmission of the oxygen gas to the user through the nasal cannula in response to a signal from the detector.

It is yet another aspect of one or more embodiments of the present patent application to provide a system that includes means for transmitting oxygen gas to a user, the means for transmitting oxygen gas comprising a flexible tube configured to transmit the oxygen gas to the user, means for transmitting light having a frequency spectrum range at least including that of light resulting from combustion of the means for transmitting oxygen gas while transmitting the oxygen gas to the user, the means for transmitting light coupled to the means for transmitting oxygen gas, means for detecting the light transmitted through the means for transmitting light, the means for detecting the light operatively coupled to the means for transmitting light, and means for interrupting the transmission of the oxygen gas through the means for transmitting oxygen gas in response to a signal from the means for detecting.

It is yet another aspect of one or more embodiments of the present patent application to provide an assembly for use in a nasal cannula. The assembly includes a flexible tube configured to transmit oxygen gas to a user, and an optical fiber coupled to the flexible tube and configured to transmit light having a frequency spectrum range at least including that of light resulting from combustion of the flexible tube while transmitting the oxygen gas to the user.

These and other objects, features, and characteristics of the present patent application, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present patent application.

DETAILED DESCRIPTION OF EXEMPLARY EMBODIMENTS

Figure 1:
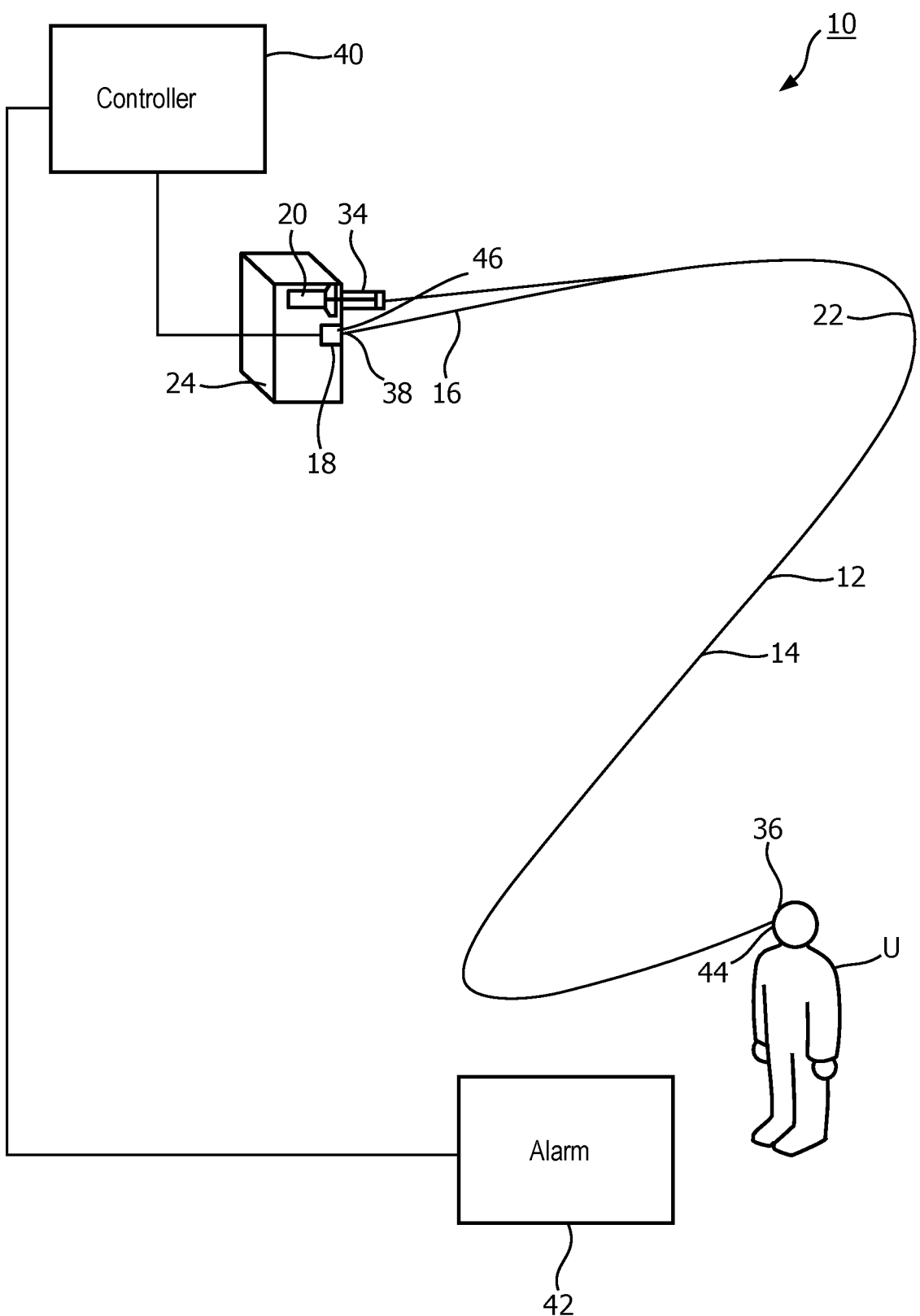
FIG. 1 is a system for detecting combustion of a nasal cannula, while transmitting oxygen gas to a user, in accordance with an embodiment of the present patent application.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 for detecting combustion of a nasal cannula 12, while transmitting oxygen gas to a user U. In one embodiment, system 10 includes nasal cannula 12 having a flexible tube 14 configured to transmit the oxygen gas to user U, an optical fiber 16 coupled to nasal cannula 12 and configured to transmit light therethrough, a detector 18 operatively coupled to optical fiber 16 and configured to detect the light transmitted through optical fiber 16, and a valve 20. The light transmitted through optical fiber 16 having a frequency spectrum range at least including that of light resulting from combustion of nasal cannula 12 while transmitting the oxygen gas to user U. The valve 20 is configured to be actuated to interrupt the transmission of the oxygen gas to user U through nasal cannula 12 in response to a signal from detector 18. In one embodiment, flexible tube 14 and optical fiber 16 may together be referred to as an assembly 22 for use in nasal cannula 12.

In one embodiment, nasal cannula 12 may generally be attached to user U around the user's ears or by an elastic head band. In one embodiment, flexible tube 14 of nasal cannula 12 is configured to deliver the oxygen gas to user U. In one embodiment, referring to FIGS. 1 and 1A, one end 502 (may split into one or more nozzles) of flexible tube 14 of nasal cannula 12 may be placed in the nostrils of user U.

Figure 1A:
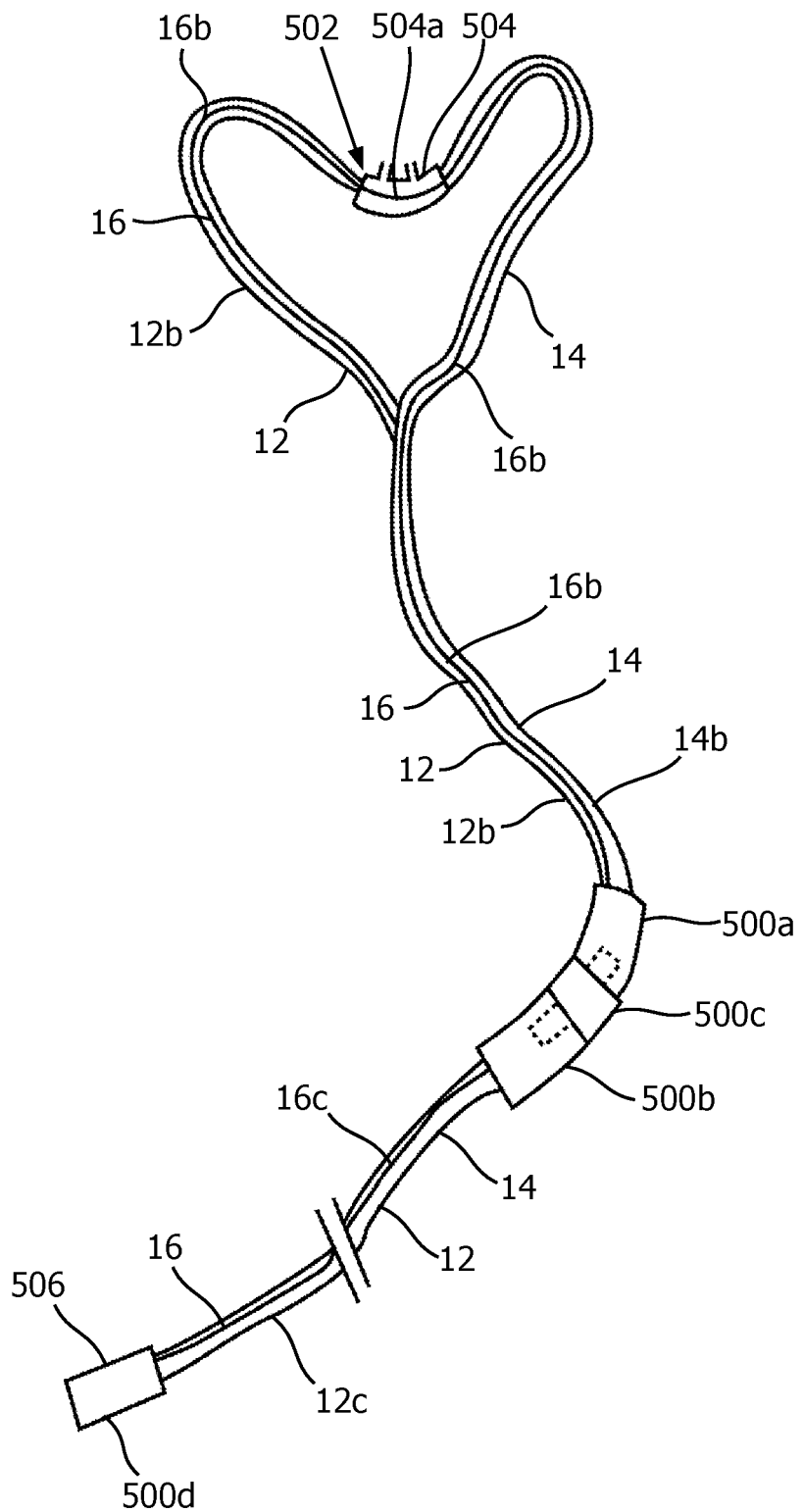
FIG. 1A shows the nasal cannula along with a flexible tubing and nasal prongs and an optical fiber coupled to the nasal cannula, in accordance with an embodiment of the present patent application.

In one embodiment, referring to FIGS. 1 and 1A, end 502 of nasal cannula 12 may include one or more nasal prongs 504. In one embodiment, optical fiber 16 may be coupled to nasal prongs 504 of nasal cannula 12. In one embodiment, as will be clear from the discussions below, optical fiber 16 coupled to nasal prongs 504 of nasal cannula 12 may be covered in a substantially opaque material to prevent light entering therein in the absence of a breach. In one embodiment, side end portions of optical fiber 16 coupled to nasal prongs 504 of nasal cannula 12 may have cap members or optical fiber connectors thereon to prevent light entering optical fiber 16 in the absence of a breach. In another embodiment, side end portions of optical fiber 16 coupled to nasal prongs 504 of nasal cannula 12 may have substantially opaque material coating thereon to prevent light entering optical fiber 16 in the absence of a breach.

In one embodiment, flexible tube 14 and optical fiber 16 may also be provided separately (by themselves) to user U or a Physician. In one embodiment, user U or the physician can choose nasal prong(s) to connect with flexible tube 14 and/or optical fiber 16. For example, in one embodiment, the present patent application includes assembly 22 for use in nasal cannula 12 and having flexible tube 14 and optical fiber 16. In one embodiment, assembly 22 may be supplied as a specialty tubing assembly to be sold separately to users that may want to use their own nasal prongs 504.

In one embodiment, other end 506 of flexible tube 14 of nasal cannula 12 may be connected to an oxygen gas source/supply 24. In one embodiment, oxygen gas source/supply 24 may be a portable oxygen concentrator or a portable oxygen generator that used to provide oxygen therapy (i.e., supplemental oxygen gas) to user U at substantially higher oxygen concentrations than the levels of ambient air.

In one embodiment, system 10 may include a cannula barb 34 that is constructed and arranged to connect to nasal cannula 12 for delivery of the oxygen gas to user U. In one embodiment, cannula barb 34 may include a connection portion that is constructed and arranged to be connected to nasal cannula 12 that transmits or delivers the oxygen gas to user U. In one embodiment, cannula barb 34 may also include a concentrator portion that is constructed and arranged to be connected to the oxygen concentrator. In one embodiment, a passage may be provided in cannula barb 34 to enable oxygen to flow therethrough.

In one embodiment, flexible tube 14 of nasal cannula 12 is made of a plastic material. In one embodiment, the materials of nasal cannula 12 may be chosen to produce a unique spectrum of light during the combustion of nasal cannula 12. In one embodiment, flexible tube 14 of nasal cannula 12 may generally be a lightweight tube having flexible configuration. In one embodiment, flexible tube 14 of nasal cannula 12 has an inner diameter ID of 4 millimeters and an outer diameter OD of 5.5 millimeters.

In one embodiment, inner diameter ID of flexible tube 14 of nasal cannula 12 may range between 3.2 and 4.8 millimeters. In one embodiment, inner diameter ID of flexible tube 14 of nasal cannula 12 may range between 3.6 and 4.4 millimeters. In one embodiment, inner diameter ID of flexible tube 14 of nasal cannula 12 may range between 3.8 and 4.6 millimeters.

In one embodiment, outer diameter OD of flexible tube 14 of nasal cannula 12 may range between 4 and 6 millimeters. In one embodiment, outer diameter OD of flexible tube 14 of nasal cannula 12 may range between 4.5 and 5.5 millimeters. In one embodiment, outer diameter OD of flexible tube 14 of nasal cannula 12 may range between 4.75 and 5.25 millimeters.

In one embodiment, referring to FIG. 1A, nasal cannula 12 may include a patient cannula 12b and a connector cannula 12c that is configured to connect patient cannula 12b to oxygen gas source/supply 24.

In one embodiment, optical fiber 16b may be coupled to patient cannula 12b. In one embodiment, optical fiber 16b extends longitudinally alongside patient cannula 12b, and is fixed to patient cannula 12b in a manner that prevents relative movement therebetween.

In one embodiment, the connector cannula 12c is constructed and arranged to allow user U to walk freely around their home. In one embodiment, the connector cannula 12c may generally be 50 to 100 feet long. In one embodiment, connector cannula 12c may include connectors 500c and 500d on both ends. In one embodiment, connector 500d of connector cannula 12c may be constructed and arranged to connect either directly or indirectly via another connector to oxygen gas source/supply 24. In one embodiment, connector 500b of connector cannula 12c may be constructed and arranged to connect either directly or indirectly via another connector 500c to connector 500a of patient cannula 12b.

In one embodiment, optical fiber 16c may be coupled to connector cannula 12c. In one embodiment, optical fiber 16c extends longitudinally alongside connector cannula 12c, and is fixed to connector cannula 12c in a manner that prevents relative movement therebetween.

In one embodiment, patient cannula 12b may generally be 6 or 7 feet long. In one embodiment, the lengths of patient cannula 12b and the connector cannula 12c may vary.

In one embodiment, system 10 may include optical fibers 16b and 16c. In one embodiment, connector 500c may be constructed and arranged such that connector 500c not only pneumatically connects connector cannula 12c and patient cannula 12b but also optically connects optical fibers 16c and 16b associated with connector cannula 12c and patient cannula 12b.

In another embodiment, system 10 may include only one optical fiber 16 that extends longitudinally alongside both connector cannula 12c and patient cannula 12b, and is fixed to both connector cannula 12c and patient cannula 12b in a manner that prevents relative movement therebetween.

In one embodiment, system 10 may include an optical fiber 504a coupled to nasal prongs 504. In one embodiment, optical fiber 504a coupled to nasal prongs 504 is configured to be optically connected to optical fiber 16b associated with patient cannula 12b. In one embodiment, optical fiber 504a coupled to nasal prongs 504 is configured to be optically connected to single optical fiber 16 associated with both connector cannula 12c and patient cannula 12b. In one embodiment, optical fiber 504a extends longitudinally alongside nasal prongs 504, and is fixed to nasal prongs 504 in a manner that prevents relative movement therebetween.

Optically connecting optical fibers and interfacing procedures for transmitting light signals between optical fiber(s) are generally known in the art of optical data transmission, and are, therefore, not described in detail here.

In one embodiment, optical fiber 16 is coupled to a portion of patient cannula 12b of nasal cannula 12. In one embodiment, optical fiber 16 is coupled to a portion of connector cannula 12c of nasal cannula 12. In one embodiment, optical fiber 16 is coupled to portions of both patient cannula 12b and connector cannula 12c of nasal cannula 12. In one embodiment, by extruding a low cost plastic optical fiber along connector cannula and continuing this optical fiber into the patient cannula area and by providing a connection between optical fiber 16 and detector 18, a cannula fire anywhere along nasal cannula 12 may be detected. That is, in one embodiment, the use of optical fiber 16 is configured to allow fire detection along the entire length of nasal cannula 12.

In one embodiment, optical fiber 16 has a small diameter and/or a small surface area so that optical fiber 16 is configured to burn as quickly as flexible tube 14 of nasal cannula 12. In one embodiment, optical fiber 16 is made of a plastic material. In another embodiment, optical fiber 16 is made of a glass material. In another embodiment, optical fiber 16 is made of a material that may be easily be burnt during the combustion of nasal cannula 12. In one embodiment, optical fiber 16 is a low cost plastic light guide fiber extruded as part of nasal cannula 12. In one embodiment, optical fiber 16 made of a glass material has an outer diameter OOD less than an outer diameter OOD of optical fiber 16 made of a plastic material so that the glass material optical fiber is configured to burn as quickly as the plastic material optical fiber.

In one embodiment, optical fiber 16 has outer diameter OOD of 1 millimeter. In one embodiment, outer diameter OOD of optical fiber 16 may generally range between 0.8 and 1.2 millimeters. In one embodiment, outer diameter OOD of optical fiber 16 may generally range between 0.9 and 1.1 millimeters. In one embodiment, outer diameter OOD of optical fiber 16 may generally range between 0.95 and 1.05 millimeters.

In one embodiment, optical fiber 16 is constructed and arranged to be small enough (i.e., has a small diameter) and/or combustible (i.e., made of a combustible material) enough so that optical fiber 16 burns at the same rate or faster than flexible tube 14 of nasal cannula 12.

In one embodiment, optical fiber 16 is constructed and arranged to be able to transmit the light from the combustion of nasal cannula 12 (i.e., a cannula fire) even though it itself is burning. In one embodiment, the light from the combustion of nasal cannula 12 (i.e., a cannula fire) is still detectable from optical fiber 16 that itself is also burning.

In one embodiment, optical fiber 16 is covered in a substantially opaque material to prevent light entering therein in the absence of a breach. That is, in one embodiment, optical fiber 16 is covered in a substantially opaque material to shield optical fiber 16 from normal ambient light surrounding optical fiber 16. In one embodiment, nasal end of optical fiber 16 is covered in a substantially opaque material.

In one embodiment, the substantially opaque material coating on optical fiber 16 is configured not to allow light to enter optical fiber 16 under normal conditions. In one embodiment, during the combustion of nasal cannula 12 anywhere along nasal cannula 12 and/or optical fiber 16, the light from the combustion of nasal cannula 12 enters optical fiber 16. In one embodiment, the light from the combustion of nasal cannula 12 would be transmitted via optical fiber 16 and immediately detected by detector 18, which would allow the oxygen flow to be shut off allowing the combustion of nasal cannula 12 to extinguish before further damage or injury occurs.

In one embodiment, optical fiber 16 includes side end portions 36 and 38. In one embodiment, side end portions 36 and 38 of optical fiber 16 are covered or coated in a substantially opaque material to prevent light entering optical fiber 16 in the absence of a breach. In one embodiment, side end portions 36 and 38 of optical fiber 16 have cap members 44, 46 thereon to prevent light entering optical fiber 16 in the absence of a breach. In one embodiment, cap members 44, 46 may be referred to as optical fiber connectors that are configured to shield optical fiber 16 from ambient light. In one embodiment, cap members 44, 46 may be fiber connectors supplied by 3M.

Figure 2:
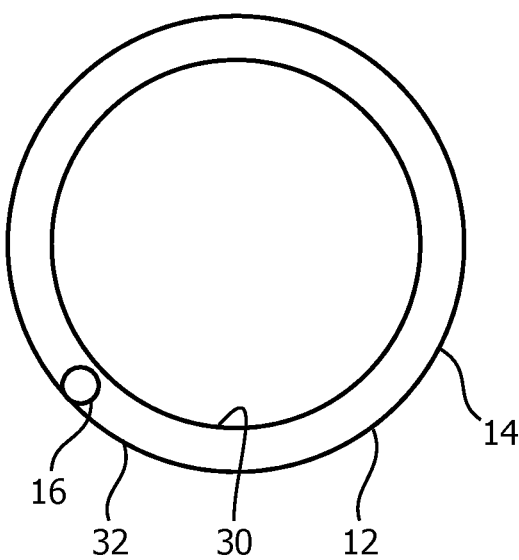
FIGS. 2, 3 and 4 show various configurations in which an optical fiber is being coupled to the nasal cannula in accordance with embodiments of the present patent application.

In one embodiment, optical fiber 16 is fixedly attached to nasal cannula 12 in a manner that prevents relative movement therebetween. In one embodiment, optical fiber 16 extends longitudinally alongside flexible tube 14, and is fixed to flexible tube 14 in a manner that prevents relative movement therebetween. In one embodiment, referring to FIG. 2, optical fiber 16 is constructed and arranged to be extruded along nasal cannula 12 and/or flexible tube 14 of nasal cannula 12.

Figure 3:
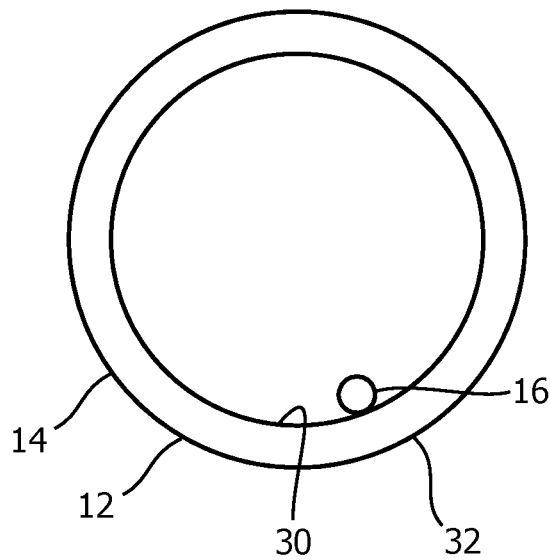
Figure 4:
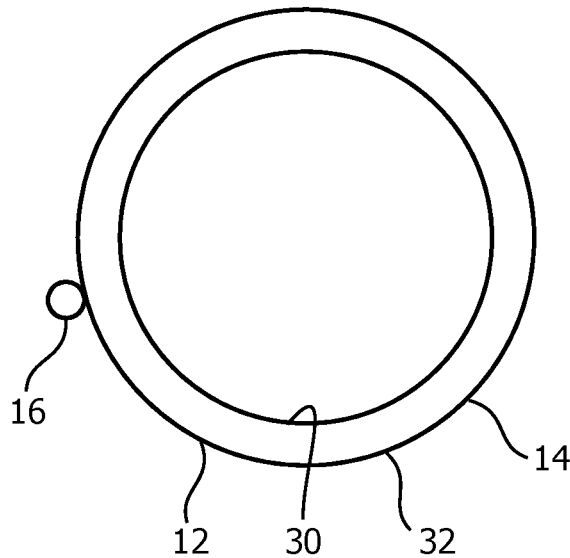

In one embodiment, referring to FIGS. 3 and 4, optical fiber 16 is constructed and arranged to be attached to either an inner wall 30 or an outer wall 32 of flexible tube 14 of nasal cannula 12. In one embodiment, as shown in FIG. 4, optical fiber 16 is constructed and arranged to be attached to outer wall 32 of flexible tube 14 of nasal cannula 12. In one embodiment, as shown in FIG. 3, optical fiber 16 is constructed and arranged to be attached to inner wall 30 of flexible tube 14 of nasal cannula 12. In one embodiment, optical fiber 16 is constructed and arranged to be attached to either inner wall 30 or outer wall 32 of flexible tube 14 of nasal cannula 12, for example, using a heat welding procedure or any other attachment procedures as would be appreciated by one skilled in the art.

In one embodiment, optical fiber 16 may form a loop with or around nasal cannula 12 and return to oxygen gas source/supply 24 allowing a light source and light detector 18 to be located on or in oxygen gas source/supply 24.

In one embodiment, detector 18 may be positioned at a proximal end of optical fiber 16. In one embodiment, detector 18 may be a photo detector, a photo sensor, an ambient light sensor (e.g., sensitive to visible, infrared (IR) and ultraviolet (UV) light) or any other fiber optic detectors. In one embodiment, detector 18 may be OPT 101 monolithic photodiode and single-supply transimpedance amplifier supplied by Texas Instruments.

In one embodiment, detector 18 may include a photodiode, a photo resistor, a photo cell, or a photo transistor. In one embodiment, a property (e.g., current, voltage or resistance) of detector 18 varies depending on the amount of light striking detector 18. In one embodiment, detector 18 may be configured to output an analog signal that is proportional to the amount of the light detected. Interfacing procedures for transmitting light signals between detector(s) and optical fiber(s) are generally known in the art of optical data transmission.

In one embodiment, detector 18 may be built into oxygen gas source/supply 24. In one embodiment, detector 18 may be part of an external detection device. In one embodiment, system 10 may include one or more detectors 18 each configured to be sensitive to different wavelengths.

In one embodiment, detector 18 is operatively coupled with a controller 40. In one embodiment, communication between controllers and detector(s) 18 occurs wirelessly or via wires. In one embodiment, controller 40 is configured to detect an occurrence of the combustion of nasal cannula 12, while transmitting the oxygen gas to user U, based on an analysis of the detected light and to send, based on the detected occurrence, the signal to valve 20 to interrupt the transmission of the oxygen gas to user U through nasal cannula 12. In one embodiment, controller is configured to perform spectral analysis of the detected light.

In one embodiment, controller 40 is configured to provide information processing capabilities in system 10. As such, controller 40 may include one or more of a digital processor, an analog processor, a digital circuit designed to process information, an analog circuit designed to process information, a state machine, and/or other mechanisms for electronically processing information. Although controller 40 is shown in FIG. 1 as a single entity, this is for illustrative purposes only. In one embodiment, controller 40 includes a plurality of processing units. These processing units may be physically located within the same device, or controller 40 may represent processing functionality of a plurality of devices operating in coordination. In one embodiment, controller 40 may be configured to execute one or more computer program modules by software; hardware; firmware; some combination of software, hardware, and/or firmware; and/or other mechanisms for configuring processing capabilities on controller 40.

In one embodiment, valve 20 is generally positioned in the flow line of the oxygen gas. In one embodiment, valve 20 is normally in an open position to allow the flow of the oxygen gas from oxygen gas source/supply 24 to user U through nasal cannula 12. In one embodiment, valve 20 may be an oxygen delivery valve that may be opened for desired durations at desired frequencies (varied by controller 40) to provide pulse delivery. Alternatively, controller 40 may maintain valve 20 open to provide continuous delivery, rather than pulsed delivery. In this alternative, controller 40 may throttle valve 20 to adjust the volumetric flow rate to user U. In another embodiment, valve 20 may be separate and independent from the oxygen delivery of valve oxygen gas source/supply 24.

In one embodiment, valve 20 is configured to be automatically closed (i.e., moved from its normal open position to a closed position) to interrupt the flow of the oxygen gas from oxygen gas source/supply 24 to user U through nasal cannula 12 in the event of the combustion of nasal cannula 12. That is, in one embodiment, valve 20 may be a shut down valve that is configured to stop the flow of the oxygen gas through nasal cannula 12, for example, upon the detection of the combustion of nasal cannula 12. In one embodiment, valve 20 may be a ball or a butterfly valve that is automatically controlled based on a signal (e.g., detection of the combustion of nasal cannula 12).

In one embodiment, valve 20 may be configured to be operated by an actuator and may be referred to as an actuated valve. In one embodiment, the actuator may include a motor driven electric actuator, a spring return pneumatic actuator or a double acting pneumatic actuator. For example, the actuator may be configured to control the opening and closing of valve 20. In one embodiment, the actuator opens or closes valve 20 based on signals sent to/received by the actuator.

In one embodiment, valve 20 may be an electronic valve operated by controller 40. For example, valve 20 may be a normally open pilot solenoid valve configured to be closed by controller 40 when controller 40 detects the combustion of nasal cannula 12. However, it should be appreciated that these examples are not intended to be limiting and valve 20 may have other configurations or take other forms in other embodiments.

In one embodiment, system 10 is configured to provide an extra precaution against a false positive detection from causing inadvertent ceasing of oxygen therapy. For example, in one embodiment, detector 18 and/or controller 40 are configured to detect the decrease in light due to the stopping of the oxygen gas. If this reduction in light is in sync with stopping of the oxygen gas, this provides a further feedback to system 10 that the light detected is from the combustion of nasal cannula 12 (i.e., a cannula fire). That is, in one embodiment, when valve 20 shuts off the oxygen gas, the detection of a reduction of light allows for increased ability to insure that the light detected is from the combustion of nasal cannula 12 (i.e., a cannula fire).

In one embodiment, when optical fiber 16 is positioned on or in nasal cannula 12, detector 18 and/or controller 40 are configured to pulse valve 20 once the combustion of nasal cannula 12 (i.e., a cannula fire) is detected. In one embodiment, detector 18 and/or controller 40 are also configured to detect the resulting "in-sync" light reduction which further increases the confidence that the light is resulting from the combustion of nasal cannula 12 (i.e., a cannula fire).

In one embodiment, system 10 may also be configured to discriminate the combustion of nasal cannula 12 from the spectra of "standard" light sources. In one embodiment, system 10 may include two detectors/optical sensors (each sensitive to different wavelengths) to discriminate the combustion of nasal cannula 12 from the spectra of "standard" light sources. In one embodiment, controller 40 of system 10 may be configured to determine a ratio of values obtained from the two detectors/optical sensors to discriminate the combustion of nasal cannula 12 from the spectra of "standard" light sources or normal ambient light.

In one embodiment, system 10 may also be configured to discriminate the combustion of nasal cannula 12 from the spectra of other open flames (e.g., candles, open fireplaces, etc.). In one embodiment, system 10 may use three detectors/optical sensors (each sensitive to different wavelengths) to discriminate the combustion of nasal cannula 12 from the spectra of other open flames (e.g., candles, open fireplaces, etc.). In one embodiment, controller 40 of system 10 may be configured to compare the values obtained from the three detectors/optical sensors to discriminate the combustion of nasal cannula 12 from the spectra of other open flames (e.g., candles, open fireplaces, etc.).

In one embodiment, system 10 may also include an alarm 42 that is configured to alert user U that a cannula fire/combustion of nasal cannula 12 has been detected and the flow of oxygen gas has been stopped. In one embodiment, alarm 42 is configured to alert the user that a breach in the substantially opaque material of optical fiber 16 is detected. In one embodiment, alarm 42 may be a visual alarm (e.g., a visual indicator or light) that is configured to alert user U that the flow of oxygen gas has been stopped. In one embodiment, alarm 42 may be an audible alarm (i.e., emit a sound) that is configured to alert user U that the flow of oxygen gas has been stopped. In one embodiment, alarm 42 may be a tactile alarm (i.e., emit vibrations) that is configured to alert user U that the flow of oxygen gas has been stopped. In one embodiment, alarm 42 may be a combination of visual, tactile and audible alarms.

In one embodiment, controller 40 may also be operatively coupled to a subject interface (not shown), which may include one or more displays and/or input devices. In one embodiment, the subject interface may be a touch-screen display. In one embodiment, the subject interface may display information regarding parameters related to the operation of portable oxygen concentrator and/or allow the subject to change the parameters, e.g., turn portable oxygen concentrator on and off, change dose setting or desired flow rate, etc. In one embodiment, communication between controller 40, portable oxygen concentrator and/or subject interface occurs wirelessly or via wires. In one embodiment, a visual alarm or indication may be provided to user U on the subject interface notifying that the combustion of nasal cannula 12 has been detected and the flow of oxygen gas has been stopped.

In one embodiment, optical fiber 16 of system 10 may also be used to communicate data to and from user U. In one embodiment, visible light may be transmitted through to optical fiber 16 of system 10 to convey information to or from user U. In one embodiment, data may be transmitted through optical fiber 16 for remote control of oxygen source/supply 24 or as a remote alarm feature. In one embodiment, these elements/functions would be additional features to the fire detection functionality of optical fiber 16.

In one embodiment, system 10 may also include an optical Time Domain Reflectometer circuit that is configured to transmit a pulse of light through optical fiber 16. In one embodiment, this configuration could be used to transmit and determine distance to the end of optical fiber 16. In one embodiment, this configuration could also be used to detect high loss spots along the optical fiber 16 to detect breaks due to cannula fire or kinking of nasal cannula 12.

In one embodiment, system 10 may also be configured to transmit a light signal through optical fiber 16 of nasal cannula 12 and to detect the light through optical fiber 16 of nasal cannula 12 from the light signal. In one embodiment, controller 40 and/or detector 18 are configured to detect this light signal. If controller 40 and/or detector 18 detect that this light signal is not continuous (or broken) for any reason, then controller 40 and/or detector 18 are configured to shut off valve 20 to stop the flow of the oxygen gas through nasal cannula 12. In one embodiment, controller 40 and/or detector 18 are also configured to activate alarm 42 to alert the user that a breach in nasal cannula 12 is detected.

Figure 5:
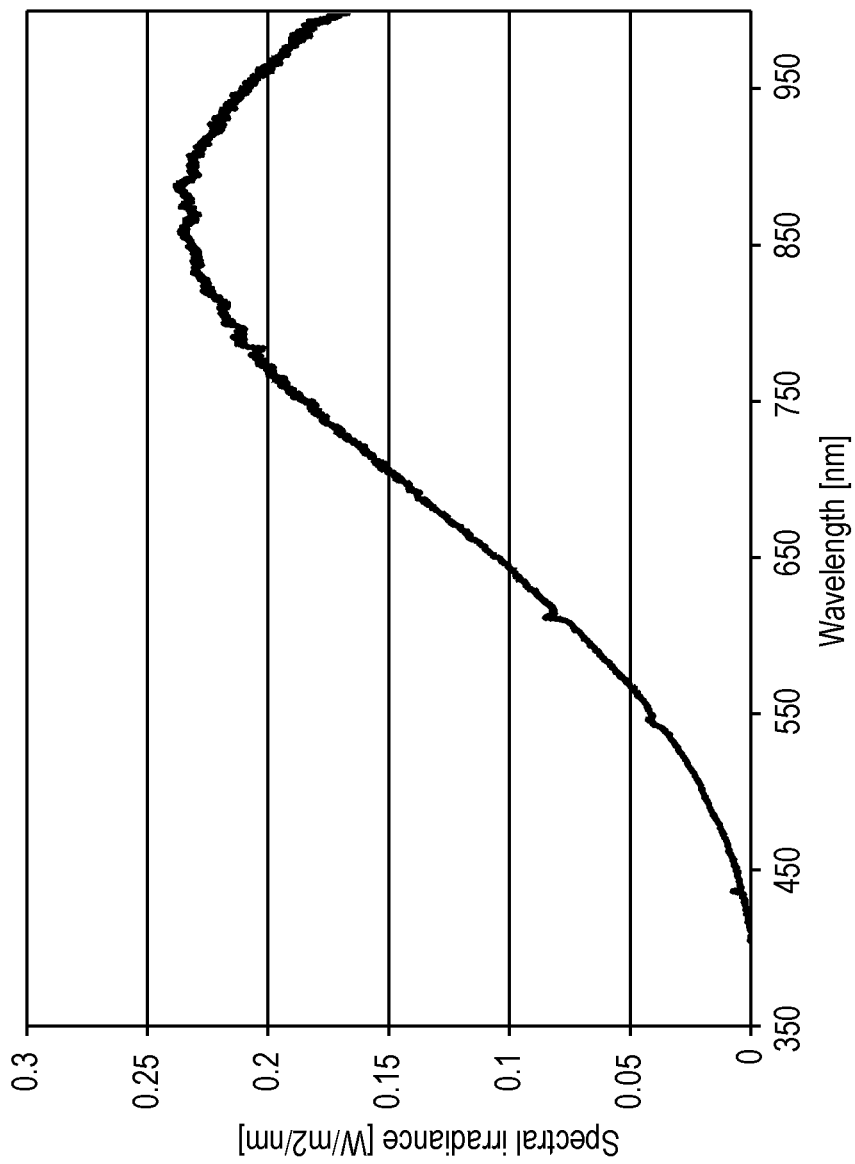
FIGS. 5 and 6 are graphical illustrations of light spectrum measurements during combustion of the nasal cannula, while transmitting the oxygen gas to the user, in accordance with an embodiment of the present patent application.
Figure 6:
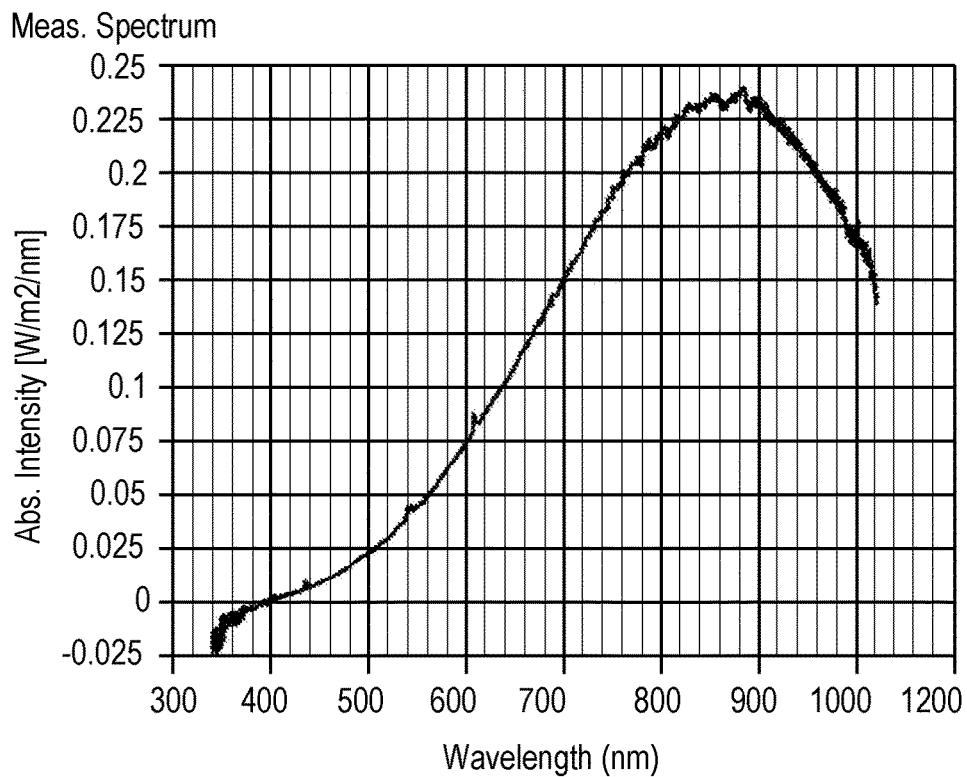

FIGS. 5 and 6 show graphical illustrations of light spectrum measurements during combustion of nasal cannula 12, while transmitting the oxygen gas to user U. The graphs in FIGS. 5 and 6 illustrate spectral irradiance or absolute intensity values on their horizontal x-axes and wavelength values on their vertical Y-axes. The spectral irradiance values are generally measured in watt per square meter per nanometer ($Wm^{-2}$ $nm^{-1}$) and the wavelength values are generally measured in nanometers (nm). FIGS. 5 and 6 show the spectral irradiance of the combustion of nasal cannula 12, while transmitting the oxygen gas to user U.

Figure 7:
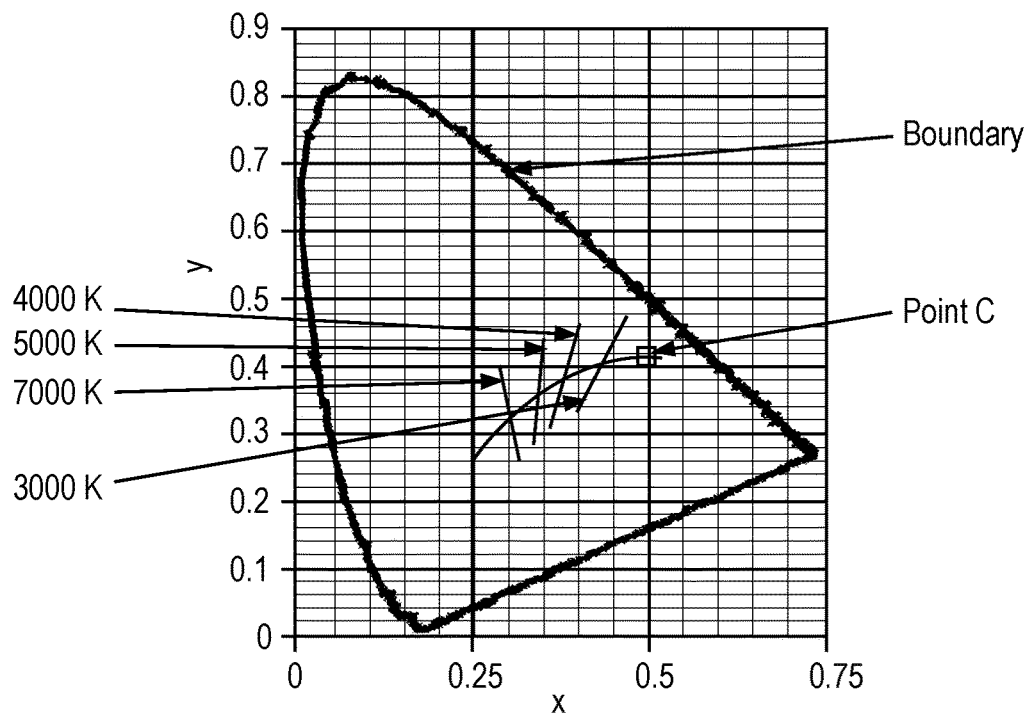
FIG. 7 shows a graphical illustration of color triangle measurements during combustion of the nasal cannula, while transmitting the oxygen gas to the user, in accordance with an embodiment of the present patent application.

FIG. 7 shows a graphical illustration of color triangle during combustion of nasal cannula 12, while transmitting the oxygen gas to user U. The graph in FIG. 7 illustrates the CIE 1931 x, y chromaticity space, showing color temperature measurements during the combustion of nasal cannula 12. The color temperature is generally measured in absolute temperature, Kelvin (K). In one embodiment, four isotemperature lines are plotted on the chromaticity diagram of FIG. 7, each (starting from the left side of the color triangle) having absolute temperatures of 7000 K, 5000 K, 4000 K, and 3000 K, respectively. In one embodiment, color correlated temperature (CCT) of the combustion of nasal cannula 12 is represented by Point C (a small square) shown in FIG. 7. The point C lies to the right of the 3000 K isotemperature line at chromaticity coordinates (x, y) of (0.5, 0.42). In one embodiment, the combustion of nasal cannula 12 has a color correlated temperature (CCT) of 2291 K at a color rendering index (CRI) of 99.5.

In one embodiment, measuring equipment having Ocean Optics USB2000+ spectrometer attached to a glass optical fiber was used to obtain the data/measurements shown in FIGS. 5-7. Referring to FIGS. 5-6, light spectrum of burning nasal cannula 12 is generally continuous (small peaks in the light spectrum are due to the fluorescent tube lighting in the room where measurements were conducted). In one embodiment, the combustion of nasal cannula 12 has a color temperature of generally around 2300 K (reddish white). Referring to FIGS. 5-6, a lot of light spectrum of burning nasal cannula 12 is generally near infrared (IR) range (i.e., above 760 nm) and there is a strong decrease towards the blue (i.e., near 400 nm).

Figure 8:
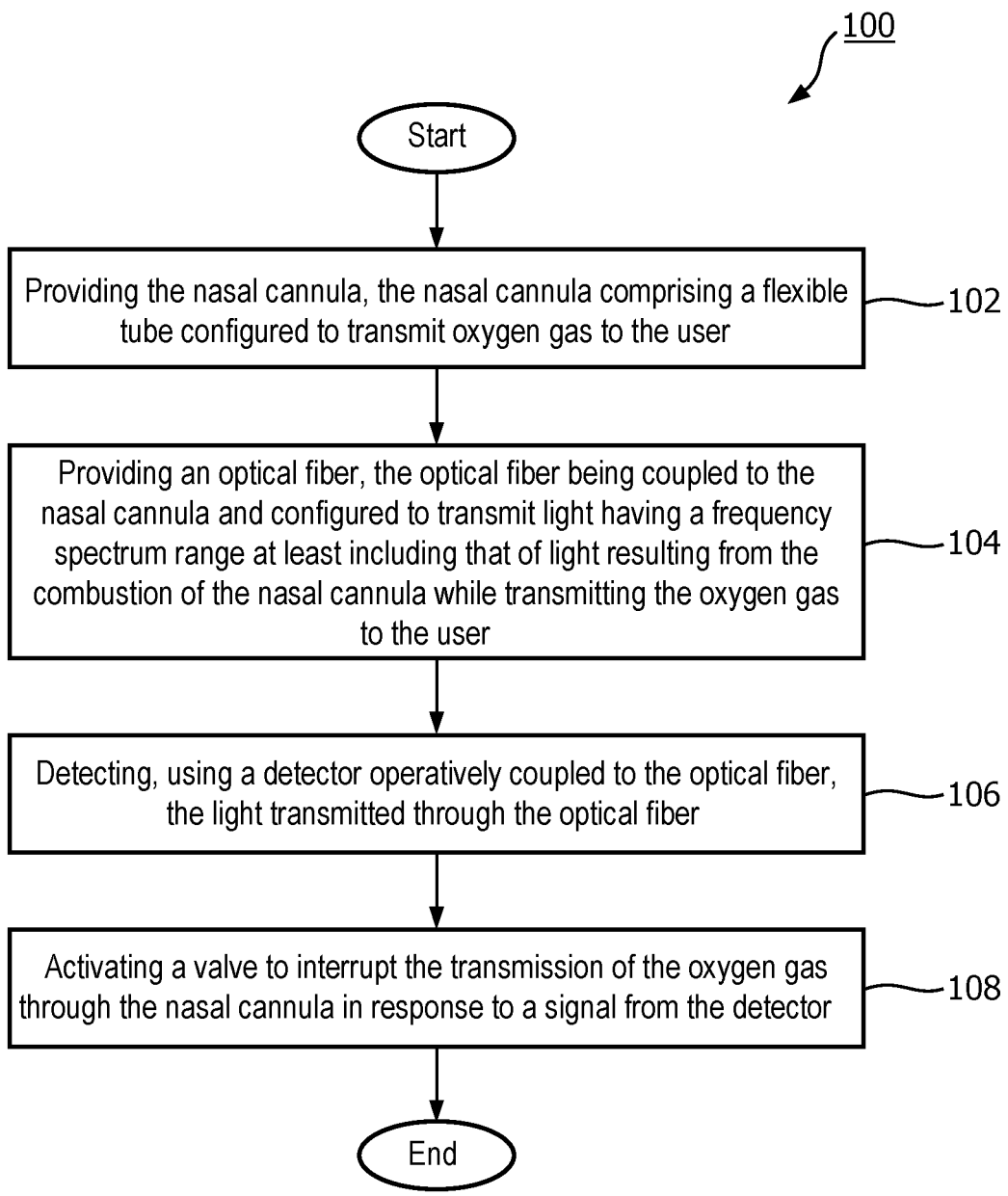
FIG. 8 is a flow chart for illustrating a method for detecting the combustion of the nasal cannula, while transmitting the oxygen gas to the user, in accordance with an embodiment of the present patent application.

FIG. 8 is a flow chart for illustrating a method 100 for detecting the combustion of nasal cannula 12, while transmitting the oxygen gas to user U. The procedures of method 100 presented below are intended to be illustrative. In one embodiment, method 100 may be accomplished with one or more additional procedures not described, and/or without one or more of the procedures discussed. Additionally, the order in which the procedures of method 100 are illustrated in FIG. 8 and described below is not intended to be limiting in anyway.

In one embodiment, method 100 may be implemented in one or more controllers or processing devices (e.g., a digital processor, an analog processor, a digital circuit designed to process information, an analog circuit designed to process information, a state machine, and/or other mechanisms for electronically processing information). The one or more controllers or processing devices may include one or more devices executing some or all of the procedures of method 100 in response to instructions stored electronically on an electronic storage medium. The one or more processing devices may include one or more devices configured through hardware, firmware, and/or software to be specifically designed for execution of one or more of the procedures of method 100.

At a procedure 102 of method 100, nasal cannula 12 is provided. In one embodiment, nasal cannula 12 includes flexible tube 14 configured to transmit oxygen gas to user (U).

At a procedure 104 of method 100, optical fiber 16 is provided. In one embodiment, optical fiber 16 is coupled to nasal cannula 12. In one embodiment, optical fiber 16 is configured to transmit light therethrough. The light having a frequency spectrum range at least including that of light resulting from combustion of nasal cannula 12 while transmitting the oxygen gas to user U.

At a procedure 106 of method 100, the light transmitted through optical fiber 16 is detected. In one embodiment, the light transmitted through optical fiber 16 is detected using detector 18 that is operatively coupled to optical fiber 16.

At a procedure 108 of method 100, valve 20 is actuated to interrupt the transmission of the oxygen gas to user U through nasal cannula 12 in response to a signal from detector 18.

In one embodiment, system 10 of the present patent application may be a standalone system that is configured to attach to a gas output of any gas source/supply, for example, an oxygen output of oxygen gas source/supply 24. In one embodiment, this standalone system may be configured to allow for attachment of optical fiber 16 and nasal cannula 12. In one embodiment, this standalone system may include detector 18 and valve 20 that is configured to shut off the flow of the oxygen gas through nasal cannula 12.

Thus, the present patent application provides a system that is configured to detect oxygen cannula fires, to help prevent serious burns to the user's face and/or body, and to prevent propagation of the fire to surrounding objects in the user's homes.

In one embodiment, the system of the present patent application may be used with oxygen concentrators, oxygen conserving devices, or any device providing flow of oxygen gas to a user. In another embodiment, the system of the present patent application may be used with any device providing flow of any flammable gas or any accelerant gas to a user through a tubing having a burnable material.

The portions and dimensions of various parts of the exemplary nasal cannula assembly and/or system as shown and described here are intended to be merely exemplary and not limiting in any way. The various parts of the exemplary nasal cannula assembly and/or system are drawn to scale in accordance with one embodiment, although other scales and shapes may be used in other embodiments. The dimensions of various parts of the exemplary nasal cannula assembly and/or system are measured in millimeters unless indicated otherwise. In one embodiment, the dimensions of various parts of the exemplary nasal cannula assembly and/or system, as shown and described here, are up to 5 percent greater than or up to 5 percent less than those illustrated and described. In another embodiment, the dimensions of various parts of the exemplary nasal cannula assembly and/or system, as shown and described here, are up to 10 percent greater than or up to 10 percent less than those illustrated and described. In yet another embodiment, the dimensions of various parts of the exemplary nasal cannula assembly and/or system, as shown and described here, are up to 20 percent greater than or up to 20 percent less than those illustrated and described.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination. [79] Although the present patent application has been described in detail for the purpose of illustration based on what is currently considered to be the most practical and preferred embodiments, it is to be understood that such detail is solely for that purpose and that the present patent application is not limited to the disclosed embodiments, but, on the contrary, is intended to cover modifications and equivalent arrangements that are within the spirit and scope of the appended claims. For example, it is to be understood that the present patent application contemplates that, to the extent possible, one or more features of any embodiment can be combined with one or more features of any other embodiment.

What is claimed is:

1. A system, comprising:
   a nasal cannula comprising a flexible tube configured to transmit oxygen gas to a user;
   an optical fiber coupled to the nasal cannula and configured to transmit light having a frequency spectrum range at least including that of light resulting from combustion of the nasal cannula while transmitting the oxygen gas to the user, wherein the optical fiber is covered or coated to inhibit light other than the light resulting from the combustion of the nasal cannula from entering the optical fiber in the absence of a breach;
   a detector operatively coupled to the optical fiber and configured to detect the light transmitted through the optical fiber; and a valve configured to be actuated to interrupt the transmission of the oxygen gas to the user through the nasal cannula in response to a signal from the detector indicating the light resulting from the combustion of the nasal cannula was detected.

2. The system of claim 1, further comprising:
a controller operatively coupled to the detector and configured to:
  detect an occurrence of the combustion of the nasal cannula, while transmitting the oxygen gas to the user, based on an analysis of detected light; and
  send, based on the detected occurrence, the signal to the valve to interrupt the transmission of the oxygen gas to the user through the nasal cannula.

3. The system of claim 2, further comprising:
an additional detector having a wavelength range sensitivity different from the detector, wherein the controller is further configured to:
  determine a ratio of values obtained from the detector and the additional detector to discriminate the combustion of the nasal cannula from spectra of standard light sources or normal ambient light.

4. The system of claim 1, wherein the optical fiber is covered or coated with a substantially opaque material to prevent light entering therein in absence of a breach.

5. The system of claim 1, further comprising:
an alarm configured to alert the user that the transmission of the oxygen gas is interrupted.

6. The system of claim 1, wherein the optical fiber is fixedly attached to the nasal cannula in a manner that prevents relative movement therebetween.

7. The system of claim 1, wherein the detector is further configured to:
output an analog signal proportional to an amount of light detected by the detector.

8. The system of claim 1, further comprising:
an oxygen gas source configured to provide the oxygen gas to the nasal cannula for transmission to the user, wherein the detector is built into the oxygen gas source.

9. The system of claim 1, wherein the detector is further configured to:
in response to the valve being actuated, detect a decrease in light, wherein the decrease in light is due to the transmission of the oxygen gas stopping to ensure that the light detected is from the combustion of the nasal cannula.

10. A method for detecting combustion of a nasal cannula while transmitting oxygen gas to a user, the method comprising:
providing the nasal cannula, the nasal cannula comprising a flexible tube configured to transmit oxygen gas to the user;
providing an optical fiber, the optical fiber being coupled to the nasal cannula and configured to transmit light having a frequency spectrum range at least including that of light resulting from combustion of the nasal cannula while transmitting the oxygen gas to the user, wherein the optical fiber is covered or coated to inhibit light other than the light resulting from the combustion of the nasal cannula from entering the optical fiber in the absence of a breach;
detecting, detecting, using a detector operatively coupled to the optical fiber, the light transmitted through the optical fiber; and
actuating a valve to interrupt the transmission of the oxygen gas to the user through the nasal cannula in response to a signal from the detector indicating that the light resulting from the combustion of the nasal cannula was detected.

11. The method of claim 10, further comprising:
detecting, using a controller operatively coupled to the detector, an occurrence of the combustion of the nasal cannula, while transmitting the oxygen gas to the user, based on an analysis of detected light; and
sending, based on the detected occurrence, the signal to the valve to interrupt the transmission of the oxygen gas to the user through the nasal cannula.

12. The method of claim 11, further comprising:
determining, using the controller and an additional detector having a wavelength range sensitivity different from the detector, a ratio of values obtained from the detector and the additional detector to discriminate the combustion of the nasal cannula from spectra of standard light sources or normal ambient light.

13. The method of claim 10, wherein the optical fiber is covered or coated a substantially opaque material to prevent light entering therein in absence of a breach.

14. The method of claim 10, further comprising:
alerting, using an alarm, the user that the transmission of the oxygen gas is interrupted.

15. The method of claim 10, wherein the optical fiber is fixedly attached to the nasal cannula in a manner that prevents relative movement therebetween.

16. A system, the system comprising:
means for transmitting oxygen gas to a user, the means for transmitting oxygen gas comprising a flexible tube configured to transmit the oxygen gas to the user;
means for transmitting light therethrough, the means for transmitting light having a frequency spectrum range at least including that of light resulting from combustion of the means for transmitting oxygen gas while transmitting the oxygen gas to the user, wherein the means for transmitting light is covered or coated to inhibit light other than the light resulting from the combustion of the means for transmitting oxygen gas to the user from entering the means for transmitting light in absence of a breach;
means for detecting the light transmitted through the means for transmitting light, the means for detecting the light operatively coupled to the means for transmitting light; and
means for interrupting the transmission of the oxygen gas through the means for transmitting oxygen gas in response to a signal from the means for detecting indicating that the light resulting from the combustion of the means for transmitting was detected.

17. The system of claim 16, further comprising:
means for:
  detecting an occurrence of the combustion of the means for transmitting oxygen gas, while transmitting the oxygen gas to the user, based on an analysis of detected light; and
  sending, based on the detected occurrence, the signal to the means for interrupting to interrupt the transmission of the oxygen gas to the user through the means for transmitting oxygen gas.

18. The system of claim 17, further comprising:
means for detecting light having a wavelength range sensitivity different from the means for detecting the occurrence of the combustion of the means for transmitting the oxygen gas and sending the signal to the means for interrupting the transmission of oxygen gas, wherein the means for detecting the occurrence of the combustion of the means for transmitting the oxygen gas and sending the signal to the means for interrupting the transmission of oxygen gas is further configured for:

determining a ratio of values obtained from the detector and the additional detector to discriminate the combustion of the nasal cannula from spectra of standard light sources or normal ambient light.

19. The system of claim 16, wherein the means for transmitting light is covered or coated with a substantially opaque material to prevent light entering therein in absence of a breach.

20. The system of claim 16, further comprising:

means for alerting the user that the transmission of the oxygen gas is interrupted.

21. The system of claim 16, wherein the means for transmitting light is fixedly attached to the means for transmitting oxygen gas in a manner that prevents relative movement therebetween.

22. An assembly for use in a nasal cannula, comprising:

a flexible tube configured to transmit oxygen gas to a user; and an optical fiber coupled to the flexible tube and configured to transmit light having a frequency spectrum range at least including that of light resulting from combustion of the flexible tube while transmitting the oxygen gas to the user, and wherein the optical fiber is covered or coated in a substantially opaque material to prevent light other than the light resulting from the combustion of the flexible tube from entering the optical fiber in absence of a breach.

23. The assembly of claim 22, wherein the optical fiber includes side end portions, wherein the side end portions are covered in a substantially opaque material to prevent light entering the optical fiber in the absence of a breach.

24. The assembly of claim 22, wherein optical fiber includes side end portions, wherein the side end portions having cap members thereon to prevent light entering the optical fiber in the absence of a breach.

25. The assembly of claim 22, wherein the optical fiber extends longitudinally alongside the flexible tube, and is fixed to the flexible tube in a manner that prevents relative movement therebetween.

26. A system, comprising:

a nasal cannula comprising a flexible tube configured to transmit oxygen gas to a user;

an optical fiber coupled to the nasal cannula and configured to transmit light having a frequency spectrum range at least including that of light resulting from combustion of the nasal cannula while transmitting the oxygen gas to the user, wherein the optical fiber is covered or coated to inhibit light other than the light resulting from the combustion of the nasal cannula from entering the optical fiber in the absence of a breach;

a first detector operatively coupled to the optical fiber and configured to detect the light transmitted through the optical fiber;

a valve configured to be actuated to interrupt the transmission of the oxygen gas to the user through the nasal cannula in response to a signal indicating the light resulting from the combustion of the nasal cannula was detected;

a second detector operatively coupled to the optical fiber and having a wavelength range sensitivity different from the detector; and a controller operatively coupled to the first detector and the second detector, wherein the controller is configured to:

determine a ratio of values obtained from the first detector and the second additional detector to discriminate the combustion of the nasal cannula from spectra of standard light sources or normal ambient light, detect an occurrence of the combustion of the nasal cannula, while transmitting the oxygen gas to the user, based on the ratio of values, and send, based on the detected occurrence, the signal to the valve to interrupt the transmission of the oxygen gas to the user through the nasal cannula.

* * * * *